United States Patent
Voigt et al.

(10) Patent No.: US 10,299,683 B2
(45) Date of Patent: May 28, 2019

(54) SYSTEM AND METHOD FOR DIFFERENTIATION OF NORMAL MYOCARDIUM FROM DIFFUSE DISEASE USING T1 MAPPING IN NON-ISCHEMIC CARDIOMYOPATHIES AND OTHERS

(71) Applicant: KONINKLIJKE PHILIPS N.V., Eindhoven (NL)

(72) Inventors: Tobias Ratko Voigt, Eindhoven (NL); Andrea Jane Wiethoff, Eindhoven (NL); Tobias Richard Schaeffter, Eindhoven (NL); Eike Caspar Cornelius Nagel, Eindhoven (NL); Valentina Otja Puntmann, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 854 days.

(21) Appl. No.: 14/385,213

(22) PCT Filed: Mar. 20, 2013

(86) PCT No.: PCT/IB2013/052223
§ 371 (c)(1),
(2) Date: Sep. 15, 2014

(87) PCT Pub. No.: WO2013/140356
PCT Pub. Date: Sep. 26, 2013

(65) Prior Publication Data
US 2015/0099964 A1 Apr. 9, 2015

Related U.S. Application Data

(60) Provisional application No. 61/613,626, filed on Mar. 21, 2012, provisional application No. 61/753,083, filed on Jan. 16, 2013.

(51) Int. Cl.
*A61B 5/00* (2006.01)
*A61B 5/055* (2006.01)
*G01R 33/56* (2006.01)

(52) U.S. Cl.
CPC ............ *A61B 5/0044* (2013.01); *A61B 5/055* (2013.01); *A61B 5/7207* (2013.01);
(Continued)

(58) Field of Classification Search
CPC ..... A61B 5/0044; A61B 5/748; A61B 5/7246; A61B 5/7207; A61B 5/7282;
(Continued)

(56) References Cited

U.S. PATENT DOCUMENTS

2008/0108894 A1* 5/2008 Elgavish ............... G06T 7/0012
600/420
2011/0142316 A1* 6/2011 Wang .................... G06T 11/006
382/131

OTHER PUBLICATIONS

Nacif, Marcelo Souto et al "Myocardial TI Mapping with MRI: Comparison of Look-Locker and MOLLI Sequences" Journal of Magnetic Resonance Imaging, vol. 34, 2011, pp. 1367-1373.
(Continued)

*Primary Examiner* — Joel Lamprecht

(57) ABSTRACT

A method for differentiation of normal myocardium from diffuse disease using T mapping includes acquiring one or more images of a patient by an imaging apparatus, generating a T1 map from the one or more images, defining a region of interest within the one or more images, determining the average T1 value within the region of interest, comparing the average T1 value within the region of interest to a cut-off T1 value, and determining a diagnosis of the region of interest from the comparison.

16 Claims, 6 Drawing Sheets

(52) U.S. Cl.
CPC .......... *A61B 5/7246* (2013.01); *A61B 5/7282* (2013.01); *A61B 5/7292* (2013.01); *A61B 5/748* (2013.01); *G01R 33/5601* (2013.01); *G01R 33/5602* (2013.01)

(58) Field of Classification Search
CPC .. A61B 5/7292; A61B 5/055; G01R 33/5601; G01R 33/5602
See application file for complete search history.

(56) References Cited

OTHER PUBLICATIONS

Messroghli, Daniel R. et al "Human Myocardium: Single-Breath-Hold MR T1 Mapping with High Spatial Resolution—Reproducibility Study", Radiology, vol. 238, No. 3, Mar. 2006, pp. 1004-1012.

Iles, Leah et al "Evaluation of Diffuse Myocardial Fibrosis in Heart Failure with Cardiac Magnetic Resonance Contrast-Enhanced T1 Mapping", Journal of the American College of Cardiology, vol. 52, No. 19, 2008, pp. 1574-180.5.

Xue, Hui et al "Improved Motion Correction using Image Registration based on Variational Synthetic Image Estimation: Application to Inline T1 Mapping of Myocardium" Journal of Cariovascular Magnetic Resonance, vol. 13, 2011.

Messroghli, Daniel R. et al "Modified Look-Locker Inversion Recovery (MOLLI) for High-Resolution T1 Mapping of the Heart", Magnetic Resonance in Medicine, vol. 52, 2004, pp. 141-146.

Messroghli, Daniel R. et al "Myocardial T1 Mapping: Application to Patients with Acute and Chronic Myocardial Infarction", Magnetic Resonance in Medicine, vol. 58, 2007, pp. 34-40.

Knowles, Benjamin R. et al "Pharmacokinetic Modeling of Delayed Gadolinium Enhancement in the Myocardium", Magnetic Resonance in Medicine, vol. 60, 2008, pp. 1524-1530.

Buerger, Christian et al Hierarchical Adaptive Local Affine Registration for Fast and Robust Respiratory Motion Estimation, Medical Image Analysis, vol. 15, 2011, pp. 551-564.

NG, Arnold C.T. et al "Association between Diffuse Myocardial Fibrosis by Cardiac Magnetic Resonance COntrast-Enhanced T1 Mapping and Subclinical Myocardial Dysfunction in Diabetic Patients: A Pilot Study" Circulation Cardiovascular Imaging, vol. 5, 2012, pp. 51-59.

* cited by examiner

SYSTEM AND METHOD FOR DIFFERENTIATION OF NORMAL MYOCARDIUM FROM DIFFUSE DISEASE USING T1 MAPPING IN NON-ISCHEMIC CARDIOMYOPATHIES AND OTHERS

CROSS-REFERENCE TO PRIOR APPLICATIONS

This application is the U.S. National Phase application under 35 U.S.C. § 371 of International Application No. PCT/IB2013/052223, filed on Mar. 20, 2013, which claims the benefit of U.S. Provisional Patent Application No. 61/613,626, filed on Mar. 21, 2012 and U.S. Provisional Patent Application No. 61/753,083, filed on Jan. 16, 2013. These applications are hereby incorporated by reference herein.

The present application relates to the medical arts, magnetic resonance arts, and related arts. The present application finds particular application in systems and methods pertaining to differentiation of normal myocardium from diffuse disease using T1 mapping in non-ischemic cardiomyopathies and others. However, it is to be understood that it also finds application in other applications, and is not necessarily limited to the aforementioned application.

The present application is related to U.S. application 61/613,626 (filed Mar. 21, 2012), in which exemplary embodiments of systems and methods according to the present application were disclosed and described in connection with patients with hypertrophic and dilative cardiomyopathy as exemplary applications of such exemplary systems and methods. The present application is also related to U.S. application 61/753,083 (filed Jan. 16, 2013). The entire disclosures of both U.S. applications 61/613,626 and 61/753,083 are hereby incorporated herein by reference.

While it was described in 61/613,626 that these exemplary systems and methods are suitable for many other applications, as one having ordinary skill in the art should appreciate in view of the teachings therein, 61/753,083 and the present application specifically describe how exemplary systems and methods described herein and in 61/753,083 and 61/613,626 also work in patients with systemic lupus erythematosus, for example.

Diffuse myocardial tissue generally cannot be detected with standard late gadolinium enhancement (LGE) cardiac magnetic resonance (CMR). This is because grey scales in the images have to be normalized to healthy myocardium, which is feasible in locally scarred tissue but not in diffusely diseased myocardium. Described herein is a system and method that can be used to distinguish between normal and diffusely diseased myocardium based on quantitative T1 mapping.

Diffuse fibrosis can develop under several clinical conditions. For example, exemplary systems and methods according to the present application can use T1 mapping in patients with hypertrophic and dilative cardiomyopathy. Exemplary systems and methods according to the present application can also use T1 mapping in patients with systemic lupus erythematosus. Other potential clinical applications of exemplary embodiments of system and methods according to the present application include, but are not limited to, e.g., amyloidosis, viral or toxic myocarditis and patients undergoing chemotherapy. One having ordinary skill in the art should appreciate additional applications of exemplary systems and methods according to the present application in view of the teachings herein.

As indicated above, diffuse fibrotic myocardial tissue generally cannot be detected with standard late gadolinium enhancement (LGE) cardiac magnetic resonance (CMR). Exemplary system and methods according to the present application provide a way to solve this problem.

Various studies have tested T1 mapping as a predictor in heart failure patients after administration of a MRI contrast agent. This has several limitations which can be overcome by the exemplary system and method described herein, such as, T1 mapping can be affected by a variety of independent variables including renal function, contrast type and dose of administration, variation in sampling time-points in study protocol and individual pharmacokinetics. Patients with contra indication to contrast administration would likely have to be excluded. Additionally, post-contrast T1 values imaging at the rigid time-points can prove cumbersome in clinical routine. For example, one previous study used T1 mapping in patients with heart failure but showed no significant difference in native T1 values, which highlights the necessity of an exemplary system and method as described herein.

The present application provides new and improved systems and methods for differentiation of normal myocardium from diffuse disease using T1 mapping in non-ischemic cardiomyopathies and others which overcomes the above-referenced problems and others.

In accordance with one aspect, a method for differentiation of normal myocardium from diffuse disease using T1 mapping is provided. The method including acquiring one or more images of a patient by an imaging apparatus, generating a T1 map from the one or more images, defining a region of interest within the one or more images, determining the average T1 value within the region of interest, comparing the average T1 value within the region of interest to a cut-off T1 value, and determining a diagnosis of the region of interest from the comparison.

In accordance with another aspect, a magnetic resonance system is provided. The system including an imaging apparatus which acquires one or more images of a patient, a T1 mapping processor which generates a T1 map from the one or more images, and a T1 value processor which defines a region of interest within the one or more images, determines the average T1 value within the region of interest, and compares the average T1 value within the region of interest to a cut-off T1 value.

In accordance with another aspect, a magnetic resonance system is provided. The system including one or more processors programmed to acquire one or more images of a patient by an imaging apparatus, generate a T1 map from the one or more images, define a region of interest within the one or more images, determine the average T1 value within the region of interest, compare the average T1 value within the region of interest to a cut-off T1 value, and determine a diagnosis of the region of interest from the comparison.

One advantage resides in the differentiation of normal myocardium from diffuse disease using T1 mapping.

Another advantage resides in improved patient care.

Still further advantages of the present invention will be appreciated to those of ordinary skill in the art upon reading and understanding the following detailed description.

The invention may take form in various components and arrangements of components, and in various steps and arrangements of steps. The drawings are only for purposes of illustrating the preferred embodiments and are not to be construed as limiting the invention.

Figure 10:
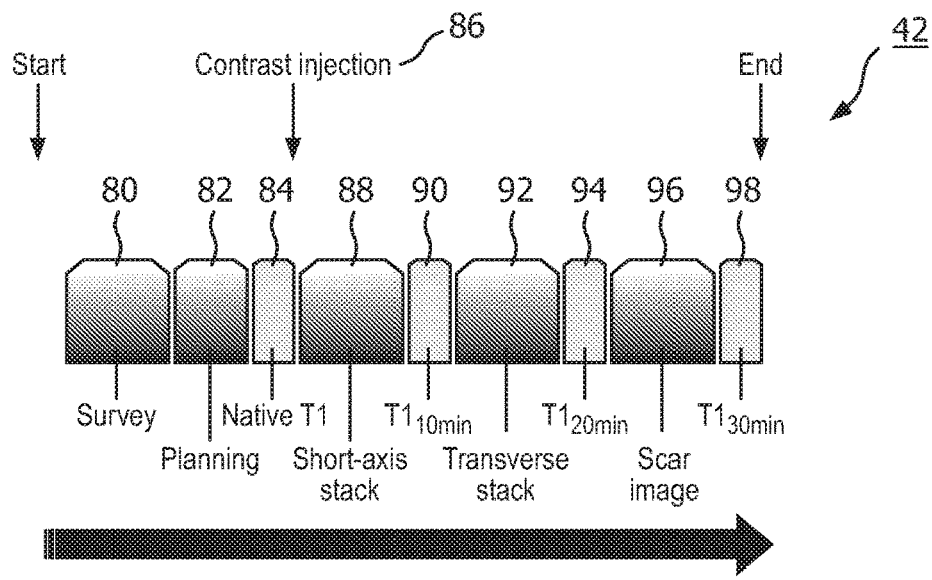

FIG. 10 diagrammatically illustrates timing of a T1 mapping sequence in accordance with the present application.

Figure 11:
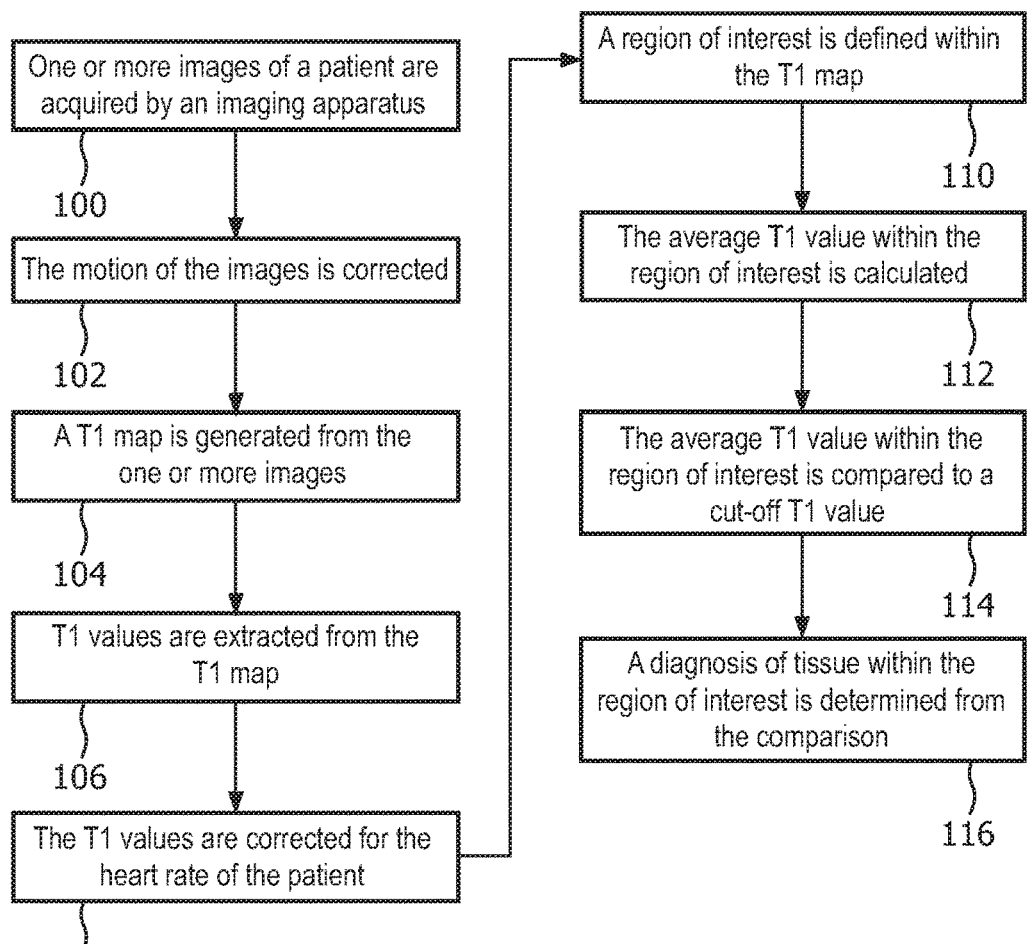

FIG. 11 is a block diagram of a method for differentiation of normal myocardium from diffuse disease using T1 mapping according to aspects of the present application.

The present application is directed to systems and methods for differentiation of normal myocardium from diffuse disease using T1 mapping in non-ischemic cardiomyopathies and others. Specifically, the systems and methods utilize the differences in T1 values generated from the T1 map to differentiate between diseased and normal tissue. To accomplish the above functionality, the systems and methods utilize CMR T1 mapping using a Modified Look-Locker Inversion-recovery (MOLLI) sequence prior and (in another exemplary embodiment) at 10, 20 and 30 minutes following contrast administration. The exemplary method does need contrast agents only in another embodiment. Rather, in another exemplary embodiment, virtually any other accurate T1 mapping sequence can be used instead of MOLLI. Motion correction is performed on the acquired images before T1 map reconstruction. In the exemplary method, the MOLLI sequence produces 11 images that can be used for T1 map reconstruction. In accordance with an exemplary method described herein, a hierarchical adaptive local affine registration (HALAR) technique can be used. In another exemplary method in accordance with the present application, virtually any other accurate motion correction technique can be used. Heart rate (HR)-correction of T1 values is then performed. One approach that can be used in accordance with exemplary embodiments of the present application is to check for a correlation between HR and T1 and then normalize T1 values to average study HR using that correlation. A region of interest (ROI) is defined for the average T1 calculation. Specifically, a ROI is drawn and average T1 and R1 calculated inside the ROI is determined. The ROI can be determined automatically in another embodiment, for example. The T1 values are then compared to cut-off T1 value to differentiate between diseased and normal tissue. In the exemplary embodiment, a cut off value of 1184 ms on native T1 maps is utilized to distinguish between diseased and normal myocardium in accordance with the present application. For example, using the exemplary method described herein, it is possible to identify the native T1 value as the independent discriminator of cardiomyopathic myocardium (p=0.001) with a sensitivity of 100%, specificity 96%, diagnostic accuracy 99%, and a positive predictive value of 98% and a negative predictive value of 100%. In connection with SLE patients, exemplary methods described herein yielded results including prolonged native T1 (cut-off value 1108 ms), providing means to detect subclinical involvement in SLE patients with high diagnostic accuracy (sensitivity of 100%, specificity 91%, diagnostic accuracy 95%), for example.

Figure 1:
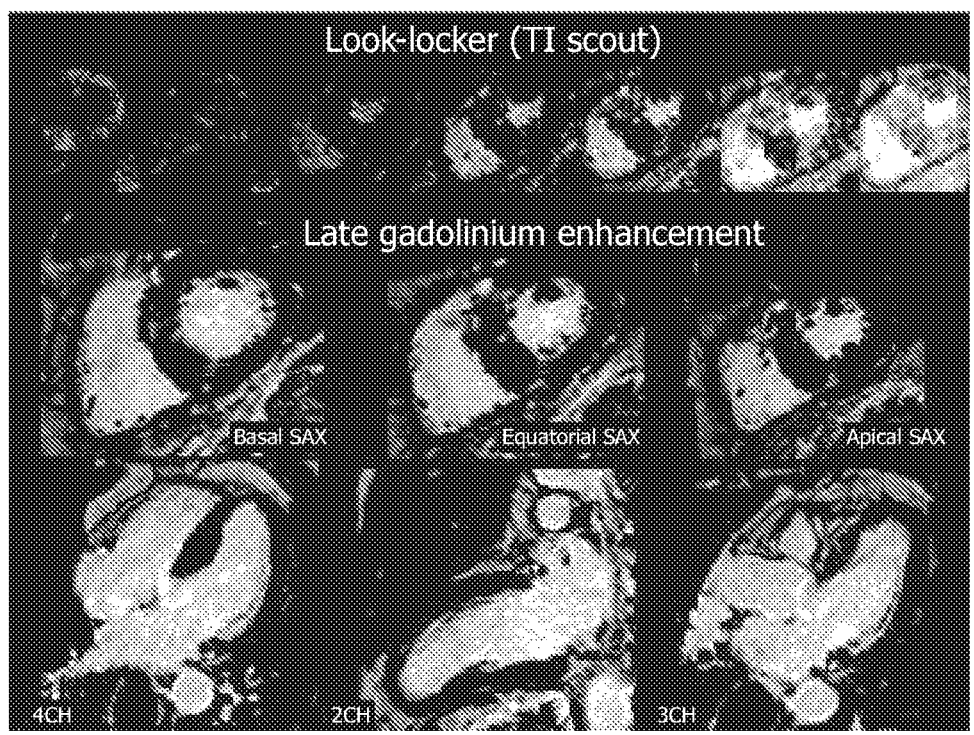
FIGS. 1-3 are exemplary illustrations of a "nulled" reference in diffuse fibrotic processes.
Figure 2:
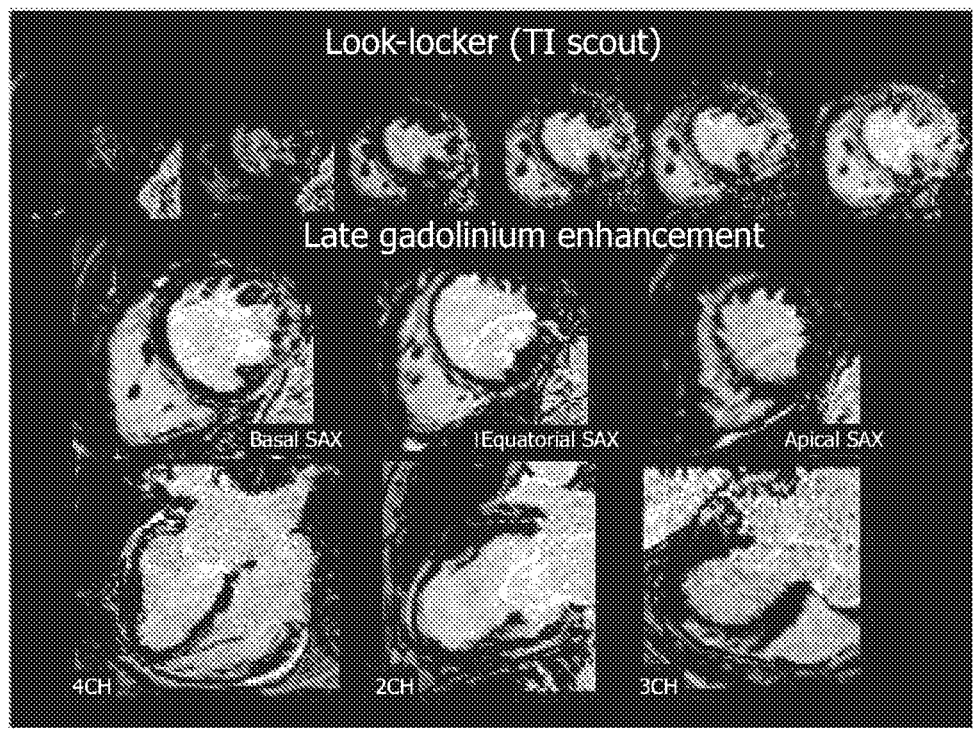
Figure 3:
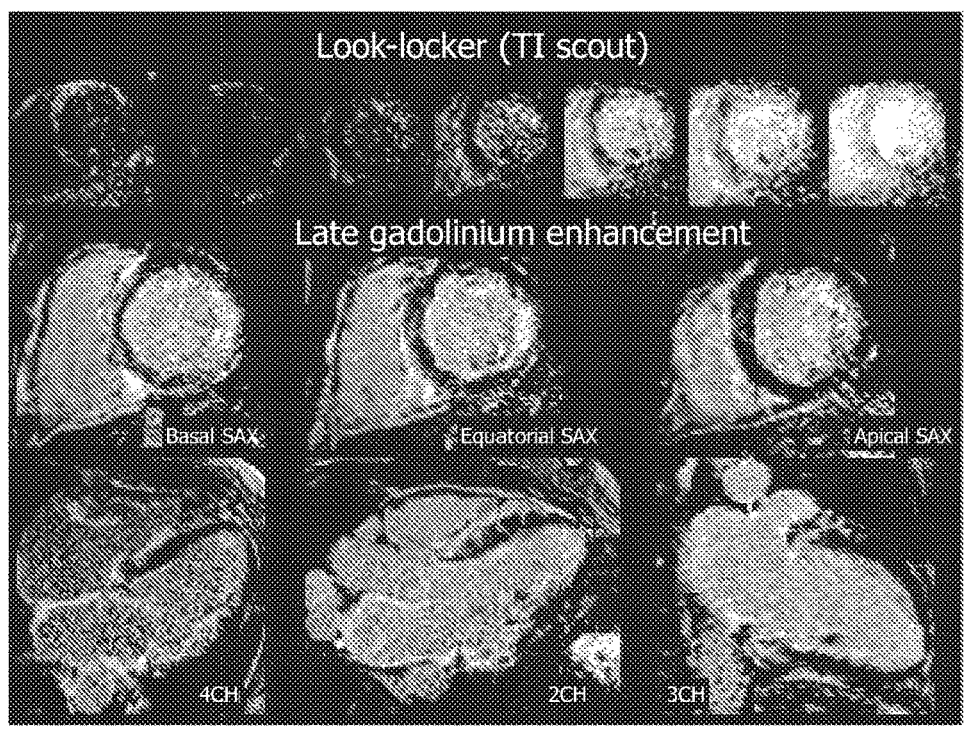

Myocardial fibrosis is a fundamental process in the development of myocardial dysfunction in various cardiomyopathies, leading to myocardial remodelling and poor outcome. Cardiac magnetic resonance (CMR) is increasingly applied as the first line investigation into the causes of cardiomyopathies. Visualisation of fibrosis by CMR is based on a greater distribution volume and slower washout of gadolinium contrast agents within tissues with greater extracellular space due to oedema or fibrosis. Whereas regional fibrosis after ischaemic injury is readily distinguished by well-delineated areas of increased signal intensity on T1-weighted images by late gadolinium enhancement (LGE), it may be impossible to define an area of clearly unaffected myocardium as a 'nulled' reference in diffuse fibrotic processes (FIGS. 1-3). As a consequence, such images may null the signal in areas of fibrosis obscuring the finding or result in images with various grey values not allowing for a clear "yes/no" decision. Recently, several studies proposed the measurement of T1 relaxation post contrast agent administration as potentially valuable for quantitative assessment of myocardial fibrosis. Following contrast administration, regional and also diffusely scarred myocardium showed shorter T1 relaxation and delayed normalization of T1 times with gadolinium washout. Whereas these observations show the potential of T1 mapping for the evaluation of myocardial fibrosis, these studies used a variety of imaging methodologies and post-processing approaches to yield a clinically robust application. The present application is directed to examining the value of native and post-contrast T1 relaxation in differentiation of healthy and diffusely diseased myocardium in two model conditions, hypertrophic (HCM) and dilated cardiomyopathy (DCM).

To demonstrate that T1 mapping provides indices with high diagnostic accuracy for the discrimination of normal and diffusely diseased myocardium, fifty-two subjects with known hypertrophic (HCM) or dilative cardiomyopathy (DCM) were enrolled (age 44±11 years) were enrolled in a study. Groups were based on the CMR findings and consisted of subjects with known HCM (n=25) and non-ischaemic DCM (n=27). Diagnosis of HCM was based on the demonstration of a hypertrophied left ventricle (LV) associated with a non-dilated LV in the absence of increased LV wall stress, or another cardiac or systemic disease that could result in a similar magnitude of hypertrophy. All HCM patients had an expressed phenotype with typically asymmetric septal hypetrophy of increased LV wall thickness, permitting an unequivocal clinical diagnosis. None of the HCM subjects showed obstructive flow phenomena. Non-ischaemic DCM was defined by an increase in LV volumes, reduction in global systolic function and absence of evidence of ischaemic LGE. Twenty-five normotensive subjects with low pretest likelihood for LV cardiomyopathy, not taking any regular medication and with normal CMR findings including a normal LV mass index served as an age and gender matched control group. Additional exclusion criteria for all subjects were the generally accepted contraindications to CMR (implantable devices, cerebral aneurysm clips, cochlear implants, severe claustrophobia) or a history of renal disease with an eGFR<30 mL/min/1.73 m$^2$.

The study integrated native and post-contrast myocardial T1 mapping into a routine imaging protocol for the determination of the underlying aetiology of cardiomyopathy. The CMR studies were performed with the patient supine using a clinical 3T scanner (Achieva TX, Philips Healthcare, Best, The Netherlands) and a 32-channel coil. After standardized patient specific planning, volumetric cavity assessment was obtained by whole-heart coverage of gapless short-axis slices. Thereafter, cine-images of 3 long-axis views (4-chamber, 2-chamber and 3-chamber view) and transverse axial views were acquired. All cine-images were acquired using a balanced steady-state free precession sequence in combination with parallel imaging (SENSitivity Encoding, factor 2) and retrospective gating during a gentle expiratory breath-hold (TR/TE/flip-angle: 3.4 ms/1.7 ms/60°, spatial resolution 1.8×1.8×8 mm). LGE imaging was performed in corresponding views in all subjects using a mid-diastolic inversion prepared 2-dimensional gradient echo sequence (echo time/repetition time/flip angle 2.0 ms/3.4 ms/25°, spatial resolution 1.8×2×10 mm reconstructed to 1.8×1.8×8 mm, with a patient-adapted prepulse delay), 20 minutes after contrast injection (gadobutrol, 0.2 mmol/kg body weight). A steady state free precession, single breath-hold modified Look-Locker Imaging (MOLLI) was used for T1 mapping, performed in an equatorial short axis slice prior and at 10, 20 and 30 minutes following contrast administration. Imaging parameters were FOV 320×320; TR/TE/flip-angle: 3.3 ms/1.57 ms/50°, interpolated voxel size 0.9×0.9×8 mm, phase encoding steps n=166, HR adapted trigger delay, 11 phases (3+3+5), as previously described.

All routine CMR analysis was performed using commercially available software (ViewForum, Extended Workspace, Philips Healthcare, The Netherlands). Endocardial LV borders were manually traced at end-diastole and end-systole. The papillary muscles were included as part of the LV cavity volume. LV end-diastolic (EDV) and end-systolic (ESV) volumes were determined using Simpson's rule. Ejection fraction (EF) was computed as EDV-ESV/EDV. All volumetric indices were normalized to body surface area (BSA).

The LGE images were visually examined for the presence of regional fibrosis. Global enhancement was defined as % of enhanced area per total short axis stack, where enhanced area was defined by 6 standard deviations (SD) from the manually selected normal area, appearing as maximally suppressed myocardium.

Figure 4:
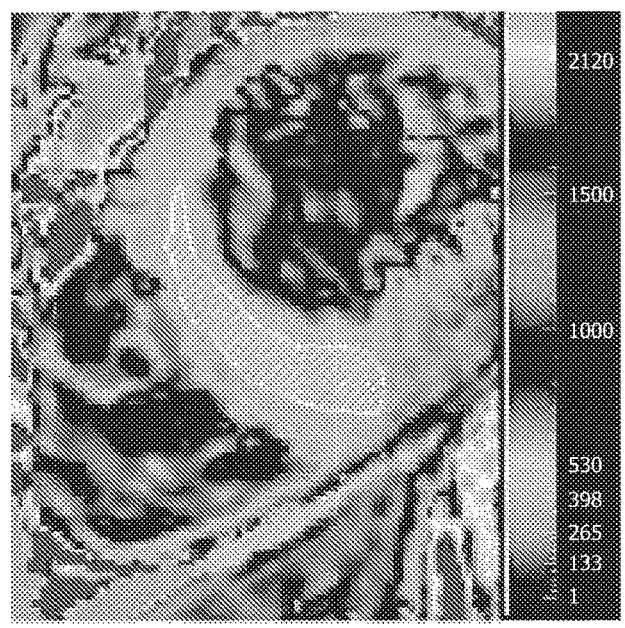
FIG. 4 is an exemplary illustration of a region of interest within the septal myocardium in accordance with the present application.
Figure 5:
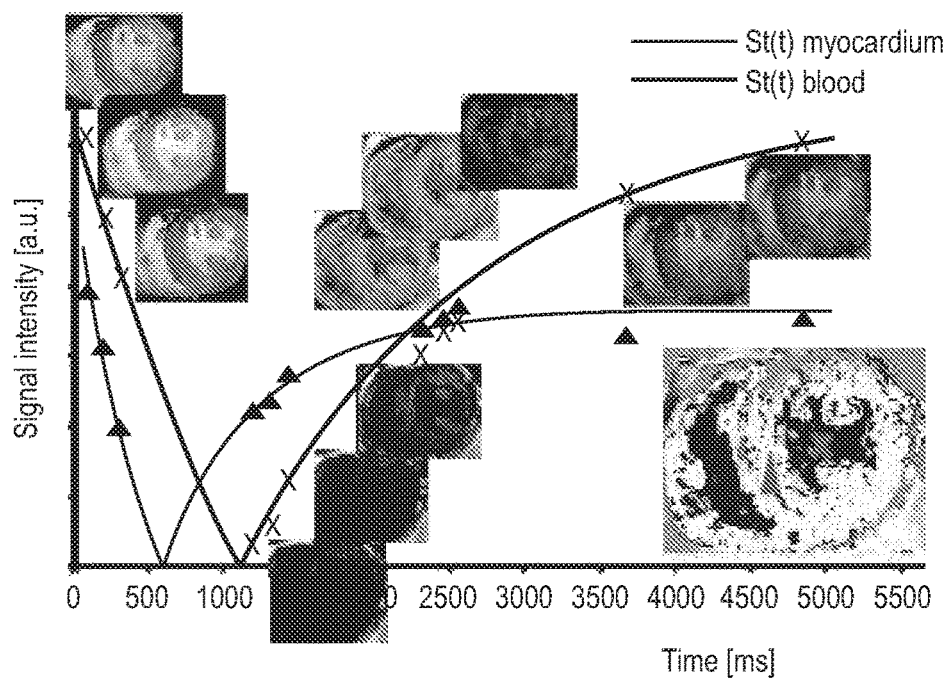
FIG. 5 is a diagrammatic illustration of the calculation of T1 values for two different tissue types in accordance with the present application.

T1 relaxation maps were obtained by RelaxMaps tools supported by PRIDE environment (Philips, The Netherlands). Whereas selective acquisition at a fixed point of the cardiac cycle in end-diastole usually largely suppressed the influence of cardiac motion, the relatively long duration of the sequence (17-heart beats to obtain a single slice map) occasionally led to some undesired breathing motion. During the study, a motion-correction image preparation step was performed using a custom-made tool developed in house based on a hierarchical adaptive local affine registration (HALAR) technique, where a reference phase (source) is registered to each of the selected target phases (11 in total). A rectangular region-of-interest (ROI) being large enough to enclose the whole of the LV is manually drawn onto the source reference phase before registration. After the initial image affine registration step of the ROI, the source image is subdivided into four smaller ROIs using equal subdivisions. Each subdivision underwent an affine transformation again (each with 6 degrees of freedom) to align the features of the target image ROIs with the corresponding ROIs in the source phase image. Co-registered images were then used to derive T1 values. Because previous studies showed substantial segmental variation in T1 values, which was the greatest in lateral and the smallest within the septal segments, a consensus was made to place the ROIs within the septal myocardium (FIG. 4). Care was also taken to avoid 'contamination' with the signal from the blood pool. Lastly, all postprocessing on T1 images was derived blinded to the presence of the any visualized scar on the LGE images to enable high inter- and intraobserver reproducibility of T1 measurements. T1 was determined by fitting a three parameter exponential model to the measured data and applying Look-Locker correction (FIG. 5). Noise was calculated in a ROI drawn manually inside the lungs and taken into account in the T1 computation. Because longitudinal relaxation is heart rate (HR)-dependent, HR-correction of T1 values was also applied when HR exceeded 80 bpm. In addition to the T1 values of myocardium and blood pool, the volume fraction of extravascular extracellular matrix (Ve) was calculated according to the formula:

$$Ve = [\lambda * (1 - hematocrit)]$$

where Ve is the myocardial extravascular extracellular volume fraction, and $\lambda = [\Delta R1 myocardium]/[\Delta R1 bloodpool]$ pre and post Gd contrast (where $R1 = 1/T1$).

Statistical analysis was performed using SPSS software (SPSS Inc., Chicago, Ill., USA, version 20.0). Differences from the control group and between the groups were examined by Student t-test or one-way ANOVA, as appropriate. Reproducibility and agreement analysis was performed using paired and unpaired Student t-test and bivariate correlations. Associations with demographic and haemodynamic variables and source of variation within the measures were explored by linear regression analyses. Binary logistic regression was used to derive the most optimal sensitivity, specificity and diagnostic accuracy of T1-derived measures in discrimination between the healthy and abnormal myocardium. The corresponding cut-off values were read off the receiver-operating characteristics (ROC) analysis table. All tests were two-tailed and a P value of less than 0.05 was considered significant.

Patients' characteristics, haemodynamics and cardiac function are presented in TABLE 1 below.

TABLE 1

Exemplary Patients' characteristics, global morphological and functional measures.

| Variable | Control (n = 30) | HCM (n = 25) | DCM (n = 27) |
| --- | --- | --- | --- |
| Gender (men, %) | 19 (63) | 16 (64) | 18 (67) |
| Age (years) | 43 ± 9 | 44 ± 11 | 45 ± 14 |
| BP systolic (mmHg) | 113 ± 6 | 115 ± 6 | 120 ± 6 |
| BP diastolic (mmHg) | 69 ± 8 | 72 ± 6 | 75 ± 10 |
| Heart rate (bpm) | 64 ± 10 | 66 ± 9 | 66 ± 9 |
| Body mass index (m/kg2) | 24 ± 3 | 24 ± 3 | 23 ± 4 |
| LV - EDV index (mL/m2) | 76 ± 9 | 70 ± 10 | 110 ± 15** |
| LV-Ejection fraction % | 63 ± 6 | 72 ± 8* | 34 ± 6** |
| LV mass index (g/m2) | 55 ± 8 | 99 ± 10** | 106 ± 11** |
| Maximal LVWT (mm) | 9 ± 2 | 18 ± 2** | 10 ± 2 |
| Global enhancement (%) | 5 ± 7 | 12 ± 9** | 11 ± 12** |
| eGFR (mL/min/1.73 m$^2$) | 82 ± 10 | 83 ± 9 | 74 ± 12 |
| Haematocrit (%) | 44 ± 3 | 43 ± 3 | 43 ± 2 |

(Student t-test for differences from the control group: *p < 0.05, **p < 0.01).

All groups had a similar gender representation, HR and BSA. In comparison to controls, HCM subjects had increased global systolic function and diastolic LV wall thickness (p<0.01). Compared to controls, subjects with DCM had increased cavity volumes and reduced global systolic function (p<0.01). Both patients' groups had increased LV mass index and global enhancement (p<0.01).

T1 values of blood pool were similar between the groups, confirming the consistency of sampling points after the weight-adapted contrast injection. T1 of native myocardium ($T1_{native}$) was significantly longer in cardiomyopathies compared to control subjects (p<0.01, TABLE 2 below). Conversely, post-contrast T1 values were significantly shorter in the presence of cardiomyopathy at all time-points (p<0.01). Similarly, lambdas were significantly lower in cardiomyopathies in comparison to controls (p<0.01). Ve values were similar at all time points for the total cohort (10 min vs. 20 min vs. 30 min: 28±11 vs. 29±10 (p=0.35) vs. 27±9 (p=0.22). Ve in patients group was significantly higher compared to controls at all time-points (p<0.01).

TABLE 2

Exemplary T1 relaxation times in native and post-contrast myocardium

| Variable | Control (n = 30) | HCM (n = 25) | DCM (n = 27) |
|---|---|---|---|
| Native | | | |
| T1 Myocardium (msec) | 1070 ± 55 | 1254 ± 43** | 1319 ± 57** |
| T1 Blood (msec) | 1892 ± 88 | 1861 ± 97 | 1914 ± 82 |
| R1 myocardium ($msec^{-1}*10^5$) | 94 ± 4 | 80 ± 4** | 76 ± 4** |
| 10 minutes | | | |
| T1 Myocardium (msec) | 402 ± 58 | 307 ± 47** | 296 ± 43** |
| T1 Blood (msec) | 253 ± 24 | 247 ± 29 | 235 ± 28 |
| $R1_{10\ min}$ myocardium ($msec^{-1}*10^5$) | 254 ± 40 | 339 ± 44** | 345 ± 41** |
| $Lambda_{10\ min}$ | 0.46 ± 0.13 | 0.72 ± 0.18** | 0.70 ± 0.18** |
| $Ve_{10\ min}$ | 0.20 ± 0.06 | 0.30 ± 0.09** | 0.29 ± 0.08** |
| 20 minutes | | | |
| T1 Myocardium (msec) | 440 ± 58 | 363 ± 63** | 355 ± 44** |
| T1 Blood (msec) | 296 ± 27 | 300 ± 37 | 292 ± 34 |
| $R1_{20\ min}$ myocardium ($msec^{-1}*10^5$) | 230 ± 31 | 284 ± 50** | 284 ± 30** |
| $Lambda_{20\ min}$ | 0.49 ± 0.12 | 0.73 ± 0.2** | 0.73 ± 0.09** |
| $Ve_{20\ min}$ | 0.20 ± 0.5 | 0.31 ± 0.10** | 0.30 ± 0.05** |
| 30 minutes | | | |
| T1 Myocardium (msec) | 504 ± 38 | 437 ± 49* | 444 ± 45* |
| T1 Blood (msec) | 360 ± 44 | 371 ± 47 | 347 ± 41 |
| $R1_{30\ min}$ myocardium ($msec^{-1}*10^5$) | 199 ± 14 | 230 ± 20** | 227 ± 23** |
| $Lambda_{30\ min}$ | 0.47 ± 0.09 | 0.67 ± 0.10** | 0.67 ± 0.12** |
| $Ve_{30\ min}$ | 0.20 ± 0.05 | 0.29 ± 0.05** | 0.28 ± 0.05** |

(Student t-test for differences from the control group: *p < 0.05, **p < 0.01).

In a subset of subjects (n=47), inter-observer mean differences (MD) for T1 values were 1.3 ms (95% CI:−12.4-15.4) for native scans and 0.7 ms (−7.9-12.3) for overall postcontrast scans, whereas intra-observer MDs were 0.3 ms (−6.3–5.3) and 0.1 (−3.4 to 4.2), respectively. The study demonstrated an excellent overall (pre- and post-contrast) intra- and inter-observer agreement in T1 values (intra-observer: r=0.99, p<0.0001; inter-observer: r=0.98, p<0.0001).

In the multivariate binary logistic regression model using native and post-contrast T1 and Ve values, the study identified $T1_{native}$ as the independent discriminator of cardiomyopathic myocardium (p=0.001) with a sensitivity of 100%, specificity 96%, diagnostic accuracy 99%, and a positive predictive value of 98% and a negative predictive value of 100%. Results of binary logistic regression and ROC analysis with cut-off values for separate T1-derived measures in differentiation of normal from abnormal myocardium are presented in TABLE 3 below.

TABLE 3

Exemplary results of univariate binary logistic regression for differentiation between normal and abnormal myocardium for sensitivity and specificity and diagnostic accuracy. The corresponding cut-off values for separate measures were derived from the receiver-operating curve analysis table: AUC (95% CI): area-under-the curve (95% confidence interval).

| Variable | Cut-off value | AUC (95% CI) | Sig. (p-value) | Specificity (%) | Sensitivity (%) | Diagnostic accuracy (%) |
|---|---|---|---|---|---|---|
| T1 value (msec) | | | | | | |
| Native | 1184 | 0.99 (0.98-1.00) | 0.000 | 98 | 100 | 99 |
| 10 minutes | 330 | 0.90 (0.87-0.97) | 0.000 | 71 | 86 | 80 |
| 20 minutes | 407 | 0.86 (0.79-0.96) | 0.000 | 71 | 82 | 77 |
| 30 minutes | 477 | 0.84 (0.74-0.96) | 0.000 | 68 | 71 | 70 |
| Ve | | | | | | |
| $Ve_{10\ min}$ | 23 | 0.86 (0.76-0.95) | 0.000 | 76 | 80 | 78 |
| $Ve_{20\ min}$ | 23 | 0.85 (0.77-0.95) | 0.000 | 72 | 82 | 78 |
| $Ve_{30\ min}$ | 23 | 0.88 (0.80-0.96) | 0.000 | 68 | 82 | 77 |

Univariate linear regression analysis for between-subject effects in the complete cohort revealed associations between $T1_{native}$ and age (F=7.8, p<0.01), and indexed LV mass (F=4.2, p=0.05), but not for HR, BP or BSA. Within the separate groups, there was a negative (non-significant) correlation between $T1_{native}$ and age (r=−0.37, p=0.09) in control group, whereas patient groups showed a positive association with age (r=0.53, p=0.03). In controls and patients with DCM, $T1_{native}$ showed associations with indexed LV-EDV (r=0.37 and 0.54, respectively, p<0.05). Patients with DCM showed further associations between $T1_{native}$ and EF (r=−0.61, p<0.01), whereas in HCM there was an association between $T1_{native}$ with indexed LV mass (r=−0.51, p<0.01). Ve values revealed strong associations with the native blood R1 (p<0.001), respective time-point blood R1 (p=0.04-0.001), and haematocrit (p<0.05), but not with age, HR, BP, LV volumes or function. There was a positive correlation between age and $Ve_{10\ min}$ (r=0.34, 0.1) in controls, and a negative association in patients group (r=−0.51, p<0.05), whereas other parameters showed no significant associations.

The study revealed that diffusely diseased myocardium can be reliably differentiated from healthy myocardium by means of T1 mapping. The study also demonstrates that native and post-contrast T1s provide indices with high diagnostic accuracy, sensitivity and specificity, with $T1_{native}$ providing the greatest distinction between healthy and diffusely diseased myocardium. The study further demonstrated that in DCM, $T1_{native}$ correlates with measures of LV remodelling and global systolic function, whereas in HCM it shows an association with indexed LV mass. The findings provide a novel and easy to use method for the detection of diffusely diseased myocardial tissue by CMR with an immediate potential for a clinical translation.

T1 mapping techniques provide quantifiable information on longitudinal relaxation through acquisition of images with different inversion times and by multi-parameter curve fitting analysis. T1 maps are derived as parametric reconstructed images, where signal intensity of a pixel depends on the absolute longitudinal relaxation properties of this voxel. Several methodologies were tested to acquire the myocardial T1 relaxation values including sets of saturation or inversion recovery images with varying inversion times, and lately, the classical and modified Look-Locker sequences. The variant of the latter sequence, which was also applied in the present study, leads to a series of multiple images acquired within the same phase of cardiac cycle through a selective fixed delay time over successive heart beats. Some studies using this or related methodologies suggested that native T1 myocardial values could be used to discern post-infarct scar from healthy myocardium. Most of these studies focused on the post-contrast T1 values and reported significantly shorter T1 times compared to controls. In a population of patients with mixed causes of heart failure, shorter T1 times were reported compared to controls even when excluding areas of regional fibrosis. These studies also observed an inverse relationship between post-contrast T1 values and amount fibrosis on histology. Ability of T1 imaging to quantify the amount of diffuse fibrosis was also confirmed by a novel technique of extracellular volume fraction imaging deriving Ve. Diastolic myocardial impairment, an indirect marker of diffuse myocardial fibrosis, was shown to correlate with abnormal post-contrast T1 values in patients with heart failure, diabetic cardiomyopathy and also amyloidosis. Whereas one previous study in patients with heart failure showed no significant difference in native T1 values, the present findings reveal for the first time that native T1 values are significantly higher in diffusely disease myocardium. The disparity with the former findings may lie in the differences in imaging techniques and higher field strength used the present study, which leads to increased values of longitudinal relaxation in native myocardium. In the present study, myocardial $T1_{native}$ provides the greatest distinction between healthy myocardium and diseased with high negative predictive value. As such it bears potential for development of easy-to-implement test in patients with suspected diffuse fibrosis, which may be missed by the classic LGE imaging. Furthermore, in subjects with low pretest likelihood for the presence of cardiomyopathy (descriptive of our control group), or in those where contrast administration is contraindicated, it may serve as an effective screening test. Lastly, future advances in sequence development that would provide whole heart coverage might potentially derive a useful approach to characterise regional differences obviating the need for contrast administration.

The observed findings in native T1 values contrast several important aspects with regards to the post-contrast T1 mapping. As gadolinium administration greatly shortens T1 values, the overall T1 tissue relaxation will depend on the dose and relaxivity of the gadolinium contrast agent, the intrinsic T1 values of the tissue and the timing of the acquisition after gadolinium administration. Post-contrast T1 sampling can thus be affected by a variety of independent variables including renal function, contrast type and dose of administration, variation in sampling time-points and individual pharmacokinetics. Post-contrast T1 values imaging at the rigid time-points can prove cumbersome in clinical routine; the study improved the inter-study comparability of the post-contrast T1 sampling by consistent time-points in our routine cardiomyopathy imaging protocol. Yet, the aforementioned influences might explain the lesser performance of post-contrast T1 values and the observed sources of variability in Ve.

In the present study T1 values were sampled in two model-conditions of diffuse myocardial fibrosis. Whereas several investigators looked at the role of T1 mapping in patients with heart failure, no previous study systematically reports T1 values in HCM. It is well established that visualisation of LGE in HCM has an important and independent prognostic implication, however, recent evidence suggests that a profibrotic state through genetically driven collagen metabolism precedes the overt phenotype with LV hypertrophy or fibrosis visible on LGE. Whether the T1-derived measures are able to detect subclinical change in collagen metabolism remains to be assessed. The study previously demonstrated that global enhancement correlates with reduction of longitudinal ventricular deformation in HCM, even when global systolic function remains apparently unaffected. Identification of early phenotypes where early fibrotic process could be quantified and followed-up prior to the effects on cardiac geometry and function would add to the management of this condition.

The observed changes in post-contrast T1 values have been previously related to increase in extracellular space, and were described by the models of acute and chronic ischaemic or inflammatory myocardial injury. The physiological correlate with diffuse myocardial pathology is less well understood; some of the aforementioned studies linked the shortening of post-contrast T1 values and increased Ve to histologically verified amount of fibrosis. The basis of extracellular matrix remodeling is influenced by the balance between the myocyte loss, and change in protein composition with either loss or excess of its hydrophilic components. Myocyte loss and atrophy of extracellular matrix due to physiological ageing may explain the negative association with age in controls, short of statistical significance in the present study. On the contrary, the accumulation of hydrophilic extracellular substrates in pathological hypertrophy or LV remodeling with increasing age and LV mass may underlie the observed increase in myocardial native T1 values.

Likewise, systemic lupus erythematosus (SLE) is a generalized inflammatory condition disease, which predominantly affects young women. Cardiovascular complications are a well recognized corollary of SLE and include inflammation of valves, myocardium and pericardium, and consequent in myocardial dysfunction and heart failure. The underlying pathology includes immune-complex and complement mediated injury with diffuse inflammation and fibrosis, and myocardial damage. It is known that cardiac injury is accelerated through bouts of active disease, however, much of this process is thought to occur as a subclinical indolent process. High prevalence of cardiovascular complications in SLE patients at younger stage with worse outcomes is well recognized, as it is not fully explained by the traditional cardiovascular risk factors, these patients are commonly missed by the routine prevention strategies. Accurate detection of early cardiac changes in subclinical stage may improve timing of preventive intervention.

Even though several imaging studies performed in SLE patients reported signs of subclinical damage and alterations of ventricular function, including alteration of diastolic function, myocardial perfusion and pericardial effusion, these signs were often nonspecific and confounded by other comorbidities. In young patients early alteration of cardiac function is likely compensated and global left ventricular (LV) function often appears preserved even as the myocardium suffers damage. In asymptomatic SLE patients several studies recorded significant impairment in LV systolic and diastolic longitudinal function. Few studies by cardiovascular magnetic resonance (CMR) recorded an increase in absolute and relative T1 and T2 signal intensity and also evidence of diffuse late gadolinium enhancement (LGE) in inferolateral wall. Further technical advances in T1-weighted tissue characterisation imaging with increased spatial resolution by CMR now enable greater insights into the myocardial function and structure by improved visualisation of myocardial fibrosis using LGE and also ability to quantify diffuse process by T1 mapping. In addition, assessment of myocardial deformation is now readily available cine imaging by feature-tracking, following the suit of speckle-tracking imaging in grey scale echocardiography. Accurate detection of subclinical changes in cardiac structure and function in SLE may allow to assess individual patients at high risk and potentially lead to improved clinical management and prognosis.

To demonstrate that T1 mapping provides the ability to detect subclinical cardiomyopathic process, thirty-seven patients with established diagnosis of SLE were enrolled in another study. All patients were in clinical remission with stable blood results and no change in medication within the previous 0.8 weeks. Sixteen normotensive subjects with low pretest likelihood for LV cardiomyopathy, taking no regular medication and with normal CMR findings including a normal LV mass index served as an age- and gender matched control group. Additional criteria of exclusion for both groups were previous history of cardiac events or known CAD or any general contraindication to contrast enhanced CMR or adenosine stress study. Patient characteristics were recorded for all the subjects, including age, gender, body mass index, renal function, presence of cardiovascular risk factors such as hypertension, diabetes mellitus, dyslipidemia and history of smoking, and cardiac and disease modifying anti-rheumatoid (DMARDS) medication.

All subjects underwent routine clinical protocol using a 3-Tesla MRI scanner (Achieva, Philips Healthcare, Best, The Netherlands) equipped with a 32-channel multi-transmit receiver cardiac coil system and an advanced CV software package (release 3.2). After standardized patient specific planning, volumetric cavity assessment was obtained by whole-heart coverage of gapless short-axis slices. Thereafter, cine-images of 3 long-axis views (4-chamber, 2-chamber and 3-chamber view) and transverse axial views were acquired. All cine-images were acquired using a balanced steady-state free precession sequence in combination with parallel imaging (SENSitivity Encoding, factor 2) and retrospective gating during a gentle expiratory breath-hold (TE/TR/flip-angle: 1.7 mssec/3.4 msec//60°, spatial resolution 1.8×1.8×8 mm). Adenosine perfusion protocol entailed up to 3 minutes of continuous adenosine infusion of 140 microgram/kg/min, where upon contrast perfusion imaging in 3 short axis slices with k-t sense sequence has been performed. LGE imaging was performed ~15 minutes after administration of contrast agent using a mid-diastolic inversion prepared 2-dimensional gradient echo sequence (TE/TR/flip-angle 2.0 msec/3.4 msec/25°, spatial resolution 1.8× 2×10 mm reconstructed to 1.8×1.8×10 mm, with a patient-adapted prepulse delay), after total dose of 0.2 mmol/kg body weight of gadobutrol. A steady state free precession, single breath-hold modified Look-Locker Imaging (MOLLI) was used for T1 mapping, performed in an equatorial short axis slice prior and at 10, 20 and 30 minutes following contrast administration. Imaging parameters were FOV 320×320; TE/TR/flip-angle: 1.57 msec/3.3 msec/50°, interpolated voxel size 0.9×0.9×8 mm, phase encoding steps n=166, HR adapted trigger delay, 11 phases (3+3+5), adiabatic prepulse to achieve a complete inversion.

All routine CMR analysis was performed using commercially available software (ViewForum, Extended Workspace, Philips Healthcare, The Netherlands). Endocardial LV borders were manually traced at end-diastole and end-systole. The papillary muscles were included as part of the LV cavity volume. LV end-diastolic (EDV) and end-systolic (ESV) volumes were determined using Simpson's rule. Ejection fraction (EF) was computed as EDV-ESVEDV. All volumetric indices were normalized to body surface area (BSA).

The LGE images were visually examined for the presence of regional fibrosis by confirmation of bright areas within myocardium in two fold-over directions and corresponding longitudinal views and by exclusion of potential artefacts. Pericardial LGE was re-confirmed by change on fold-over direction and addition of fat-suppression. It was documented and rated as none (non visible pericardium in LGE sequences), mild (faint LGE in pericardium that has signal intensity less than the signal of the ventricular blood pool), moderate (obvious enhancement that is visually similar to the ventricular blood pool) or severe (obvious significant LGE in pericardium that has signal intensity visually greater than ventricular blood pool). Maximal pericardial thickness was measured in LGE images in the short axis views.

Figure 6:
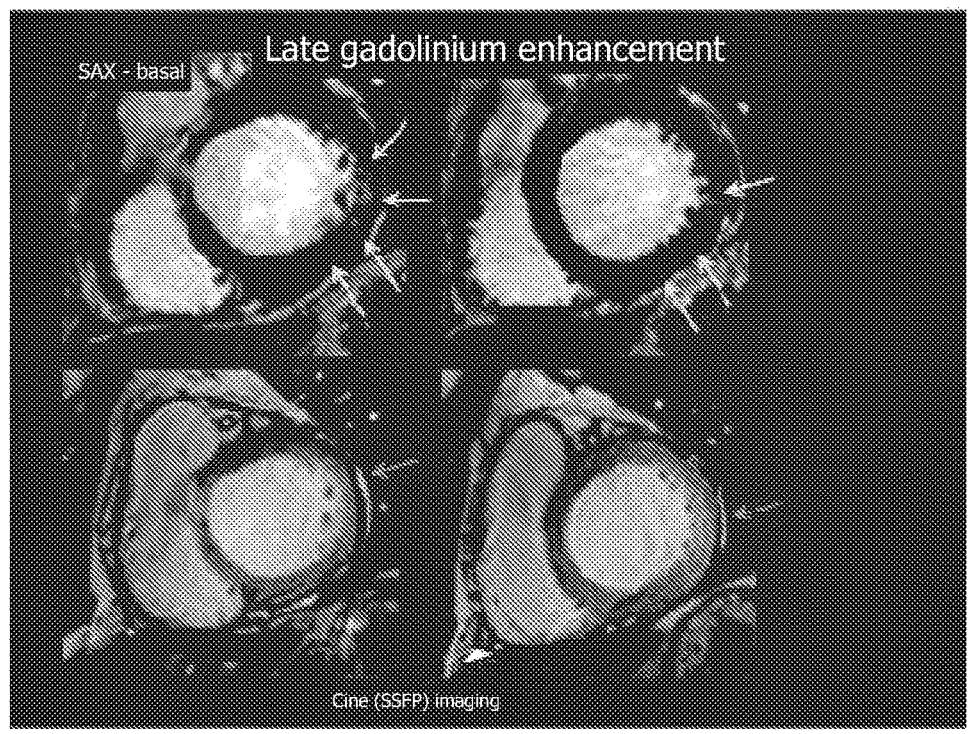
FIG. 6 is an exemplary illustration of a case with visually detectable myocardial enhancement in accordance with the present application.

T1 relaxation maps were obtained by RelaxMaps tools supported by PRIDE environment (Philips, The Netherlands) using a motion-correction image registration technique, as previously described. T1 values were obtained within the septal myocardium (FIG. 6). Care was also taken to avoid 'contamination' with the signal from the blood pool. The study additionally examined the influence of any visualized LGE on the septal ROIs for T1 values. T1 was determined by fitting a three parameter exponential model to the measured data and applying Look-Locker correction as previously described. Noise was calculated in a ROI drawn manually inside the lungs and taken into account in the T1 computation. Because longitudinal relaxation is heart rate (HR)-dependent, the study also applied HR-correction of T1 values when HR exceeded 80 bpm, as previously described. In addition to the T1 values of native myocardium and blood pool, the study calculated lambda as a surrogate index of volume fraction of extravascular extracellular matrix according to the formula:

$$\text{lambda} = [\Delta R1\text{myocardium}]/[\Delta R1\text{bloodpool}] \text{ pre and post Gd contrast} \qquad \text{a.}$$

$$R1 = 1/T1. \qquad \text{b.}$$

Deformation and rotation analysis was performed by tracing the contours within the myocardium in the cine images, using feature-tracking 2D CPA MR prototype software (TomTec GmbH, Munich, Germany), as previously described and validated. Radial and circumferential LV myocardial deformation was obtained in 3 SA slices for 16 standard segments. Longitudinal deformation was obtained in 3 long-axis views. Deformation is expressed as the average total peak-systolic strain per measured direction.

Comparisons of the means were performed by Student t-tests or chi-square test, as appropriate for the type of the data. Associations were explored by single and multivariate linear regressions with stepwise reduction of variables. Receiver-operating characteristics (ROC) analysis was used to select cut-off values to discriminate control and SLE patients. All tests were two-tailed and a P value of less than 0.05 was considered significant.

Patients' characteristics are provided in TABLE 4 below. Groups were similar for gender, age and BMI. Small number of SLE patients had traditional cardiovascular risk factors, including hypertension (n=5) and smoking (n=3), whereas none of the subjects suffered with diabetes. The average time from SLE diagnosis to imaging was 7.4 years. Fifty-nine percent of SLE patients were taking oral steroids and 47% disease modifying anti-rheumatoid medication, predominantly myocophenolatye mofetil (n=15, 41%) and hydroxychloroquine (n=6, 17%).

TABLE 4

Patient characteristics

| 1. Variable | Controls (n = 16) | SLE (n = 37) | Sig. P-value |
|---|---|---|---|
| Age (years) | 39 ± 9 | 41 ± 11 | 0.42 |
| Gender (male, n, %) | 2 (13%) | 5 (13%) | 0.99 |
| Body mass index | 24 ± 4 | 23 ± 7 | 0.61 |
| BP systolic (mmHg) | 126 ± 16 | 129 ± 20 | 0.75 |
| BP diastolic (mmHg) | 69 ± 8 | 77 ± 6 | 0.71 |
| Heart rate (bpm) | 72 ± 10 | 71 ± 8 | 0.94 |
| Smoker n, % | 1 (8%) | 3 (11%) | 0.12 |
| Diabetes Mellitus | / | 0 | / |
| Hypertension | / | 5 (13%) | / |
| Hypercholesterolaemia | / | 4 (12%) | / |
| Lupus nephritis | / | 14 (37%) | / |
| Antiphospholipid syndrome | / | 17 (46%) | / |
| ACEi/ARBs | / | 14 (37%) | / |
| Beta Blockers | / | 2 (7.4%) | / |
| Diuretics | / | 4 (12%) | / |
| Calcium channel blockers | / | 5 (13%) | / |
| Aspirin/clopidogrel | / | 3 (8%) | / |
| Statins | / | 4 (12%) | / |
| Current steroids | / | 22 (59%) | / |
| Other anti-inflammatory | / | 32 (85%) | / |
| Hb (mg/L) | 13 ± 2 | 12 ± 8 | 0.21 |
| eGFR (ml/min/m$^2$) | 71 ± 25 | 64 ± 11 | 0.35 |

Figure 7:
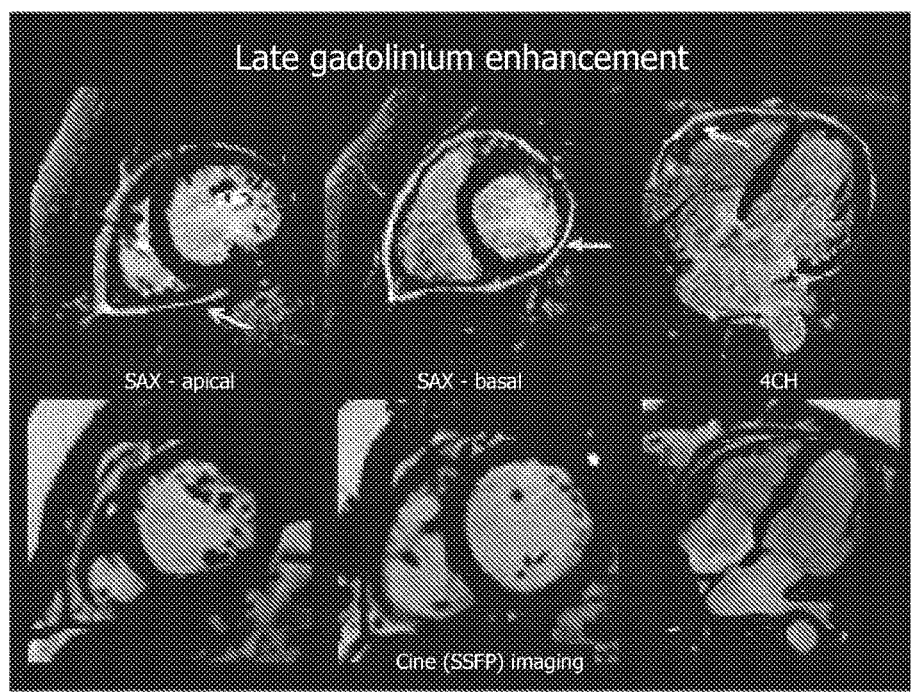
FIG. 7 is an exemplary illustration of an image of significant pericardial enhancement in accordance with the present application.

Both groups had normal volumes and global systolic function (TABLE 5: ejection fraction (%): control vs. SLE group: 60±13 vs. 56±12, p=0.57) and LV mass index (LV-mass index (g/m$^2$): 43±12 vs. 51±12 g/m$^2$, p=0.18). SLE group had significantly reduced longitudinal strain (%, −19±4 vs. −16±3, p=0.05). SLE group showed myocardial (70%) or pericardial (40%) LGE, predominantly in basal mid-ventricular inferolateral segments. T1 mapping revealed significantly increased T1 relaxation of native myocardium and lambda (p<0.01 for both). Pericardial LGE was present in 23 patients (63%), enveloping inferolateral wall and in some also globally right and left ventricle (FIG. 7). Mean pericardial thickness was 4.2±10 mm. Pericardial effusion was present in 4 patients (11%). When accounting for age, medication and duration of disease and presence or absence myocardial LGE there was no significant difference in observed values for longitudinal strain, native T1 and lambda. Similarly, the presence of visually detectable myocardial LGE showed no association with strain values, native T1 and lambda, however, there was a negative association between longitudinal strain and native T1 (r=−0.64, p=0.03) and with lambda (r=−0.57, p=0.03) in patients with SLE.

TABLE 5

Global morphological and functional measures

| Variable | Controls (n = 16) | SLE (n = 37) | Sig. P-value |
|---|---|---|---|
| LV - EDV index (mL/m2) | 76 ± 12 | 84 ± 14 | 0.11 |
| LV-Ejection fraction % | 60 ± 13 | 56 ± 12 | 0.57 |
| LV mass index (g/m2) | 43 ± 12 | 51 ± 12 | 0.18 |
| LA area (cm2) | 19 ± 4 | 20 ± 5 | 0.52 |
| Longitudinal strain | −19 ± 4 | −16 ± 3 | 0.04 |
| Radial strain | 36 ± 8 | 33 ± 9 | 0.31 |
| Circumferential strain | −24 ± 6 | −24 ± 5 | 0.99 |
| Myocardial LGE | | | |
| Present (n, %) | / | 26 (70%) | / |
| RV insertion points (n, %) | / | 15 (41%) | / |
| Intramyocardial stria (n, %) | / | 17 (46%) | / |
| Epicardial (n, %) | / | 4 (11%) | / |
| T1 mapping | | | |
| Native T1 (msec) | 1061 ± 40 | 1160 ± 56 | 0.000 |
| Lambda | 0.40 ± 0.07 | 0.55 ± 0.10 | 0.000 |
| Pericardial LGE | | | |
| Present (n, %) | / | 23 (62%) | / |
| Thickness (mm) | / | 4.2 ± 10 | / |
| Pericardial effusion (n, %) | / | 5 (14%) | / |

(Student t-test for differences from the control group: *p < 0.05, **p < 0.01).

Figure 8:
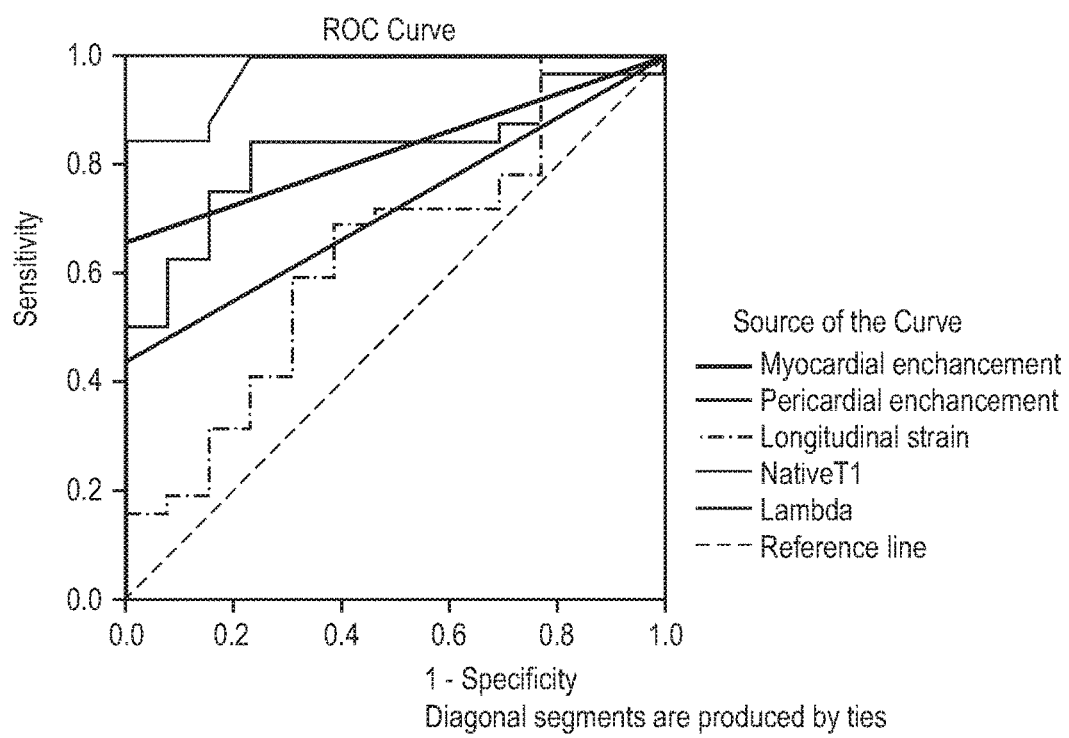
FIG. 8 is a diagrammatic illustration of receiver-operating curves for native T1, lambda, myocardial and pericardial LGE and longitudinal strain in differentiation between controls and patients.

In the multivariate binary logistic regression using myocardial and pericardial LGE, pericardial effusion, native T1, lambda and longitudinal strain, the study also identified native T1 as the independent discriminator of SLE group (chi$^2$=17, p<0.001 for the model) with a sensitivity of 100%, specificity 91%, diagnostic accuracy 95%. Addition of pericardial enhancement to native T1 in the model 2 (chi$^2$=23, p<0.001) endowed the discrimination with 100% diagnostic accuracy. Univariate and ROC analysis with corresponding cut-off values for performance of separate measures in differentiation between controls and SLE patients are presented in TABLE 6 and FIG. 8.

TABLE 6

Results of Receiver-operating curve analysis with cut-off values in differentiation of controls from SLE patients (all groups against controls), sensitivity and specificity and predictive values; AUC (95% CI): area-under-the curve (95% confidence interval).

| Variable | Cut-off value | AUC (95% CI) | Sig. (p-value) |
|---|---|---|---|
| Myocardial LGE | Present | 0.83 (0.65-1) | 0.03 |
| Pericardial LGE | Present | 0.75 (0.52-0.97) | 0.09 |
| Longitudinal strain | −0.20 | 0.72 (0.48-0.96) | 0.13 |
| Native T1 (msec) | 1108 | 0.97 (0.89-1) | 0.002 |
| Lambda | 0.51 | 0.89 (0.73-1) | 0.009 |

By using multiparametric CMR imaging, the present study demonstrates that patients with SLE have several subclinical abnormalities in cardiac structure and function despite no apparent cardiac symptoms and preserved global systolic function. The study further demonstrates that using T1 mapping provides a valid method to discern subclinical pathology in SLE patients with high diagnostic accuracy. The utility of CMR to guide and improve patients' management requires testing in future studies.

CMR is a technique that is sufficiently accurate and versatile to replicate the complexity of cardiovascular pathophysiology in patients with SLE. Detection of the small foci and striae of diffuse myocardial fibrosis by LGE complements with reduced longitudinal deformation and allows the detection of slight changes in functional performance, which are not yet manifest to global systolic function. The observed findings are concordant with the existing knowledge of histopathological changes and understanding of cardiovascular pathophysiology. One previous study using CMR in SLE patients recorded the presence of ischaemic-like myocardial LGE in patients with SLE and linked myocardial damage to the presence of CAD. The present study shows that asymptomatic SLE patients have a substantial coronary vessel wall involvement, however, without ischaemic-like LGE in myocardium. Other studies that were set to interrogate subclinical cardiovascular manifestations in the presence of systemic inflammation have shown that diffuse myocardial LGE, which is non ischaemic-like in presentation. The findings confirm the observations of diffuse perimyocardial LGE whose appearances closely resemble the aftermath of inflammatory involvement in viral myocarditis and early idiopathic cardiomyopathy, as a subacute indolent course of perimyocarditis.

Absence of ischaemic-like myocardial scar and visually normal perfusion on adenosine testing in the study further suggest that the myocardial damage in SLE can occur independently of CAD and can be directly influenced by systemic inflammation.

It is recognized that LGE can be a challenging for visualization of diffuse myocardial process, and hence, the study additionally employed quantification of T1 relaxation in native and postcontrast myocardium to assist with assessment of diffuse fibrosis. Concordant with previous observations, patients with SLE have increased native T1 relaxation. In addition, the study showed that lambda index which reflects pre and post contrast ratios of T1 relaxation times of both myocardium and blood is also increased. T1-derived indices were previously shown to correlate closely with histologically verified amount of replacement fibrosis on collagen staining Several studies demonstrated that in patients with known cardiomyopathy T1 derived measures can discriminate with high diagnostic accuracy and negative predictive value between normal and diseased myocardium. The study further expands on the previous observations by demonstrating for the first time that these measures can also discern a subclinical cardiomyopathic process. The present study demonstrates that in patients with SLE changes in T1 derived indices are independent of visualized myocardial LGE, corroborating the limitations of LGE imaging in diffusely affected myocardium. Finally, the study showed that a combination of increased native T1 and the presence of pericardial LGE, but not myocardial, is able to detect subclinical myocardial involvement with high diagnostic accuracy and negative predictive value.

In conclusion, patients with SLE have subclinical alterations in left ventricular structure and function that are unrelated to CVD. Patients with SLE have a degree of detectable perimyocardial LGE and reduced longitudinal strain, concordant with the previous knowledge of cardiovascular pathophysiology in these patients. In addition, SLE patients show prolonged T1 derived indices, including native T1 and lambda index, providing means to detect sublicinical involvement in SLE patients with high diagnostic accuracy.

Similarly, increased inflammation has been linked to myocardial dysfunction and heart failure. To demonstrate that T1 mapping provides the ability to discriminate between health and disease, a total of 37 SLE female patients subjects (mean age 41±11 years) underwent CMR for routine assessment of cardiac perfusion, function and scar. T1 mapping was performed in single short axis slice before and 15 minutes after gadolinium administration. Sixteen age-matched subjects from the clinical pool with a low pre-test probability and normal CMR acted as a control group. Both groups had normal volumes and global systolic function (ejection fraction (%): control vs. SLE group: 60±13 vs. 56±12, p=0.57) and similar LV mass index (LVmass index (g/m2): 43±12 vs. 51±12 g/m2, p=0.18). SLE patients had significantly reduced longitudinal strain (%, −19±4 vs. −16±3, p=0.05) and showed intramyocardial (70%) or pericardial (63%) late gadolinium enhancement. SLE patients had significantly increased preconstrast myocardial T1 (T1native) values and lambda (p<0.01). In comparison of significant measures, the study identified T1native as the strongest discriminator between the patients and controls.

The study demonstrated that in SLE patients without significant coronary artery disease there is evidence of subclinical perimyocardial involvement. Among variables to discern the subclinical cardiomyopathic process, T1 mapping performs best to discriminate between health and disease.

Figure 9:
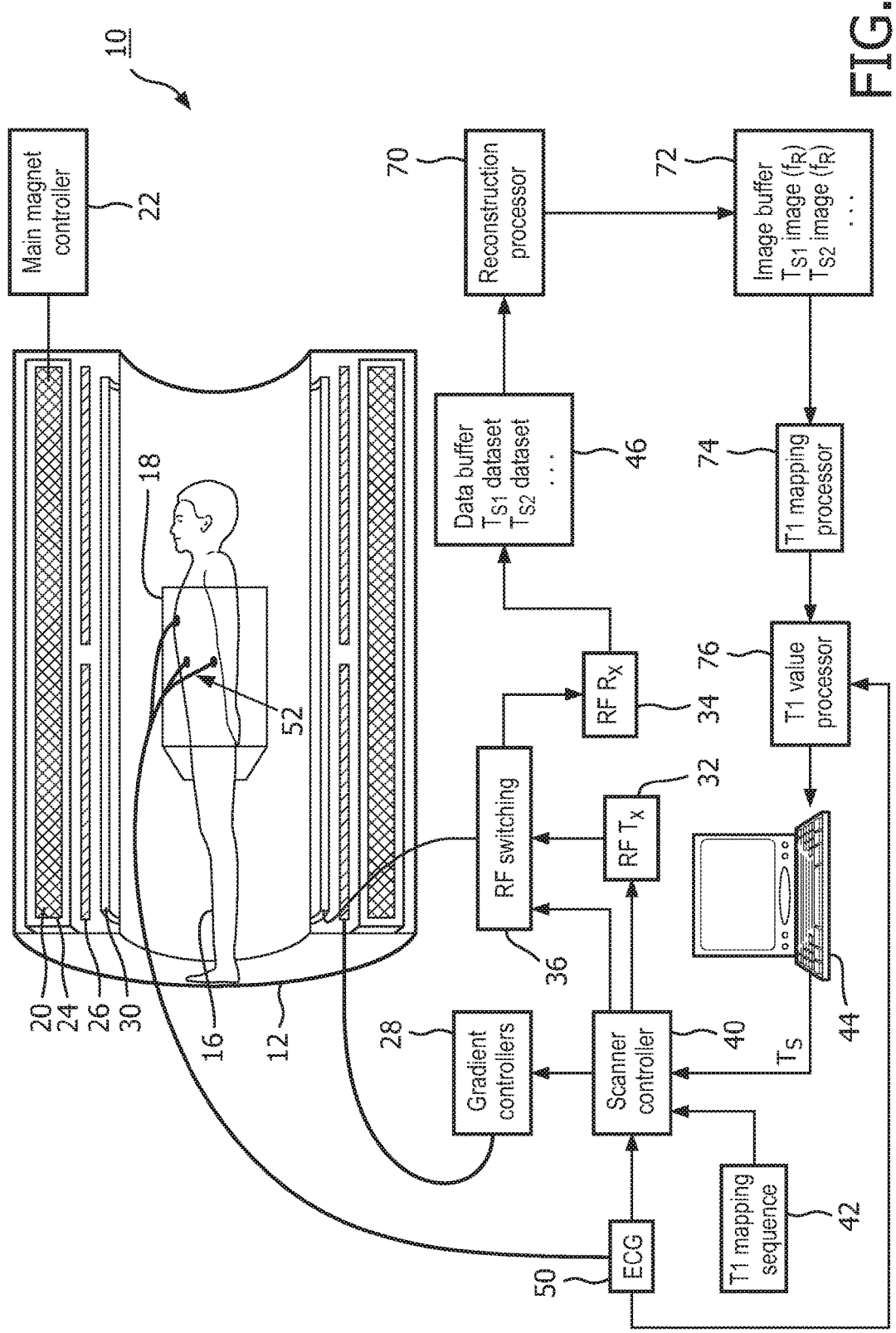
FIG. 9 is a diagrammatic illustration of a magnetic resonance imaging system in accordance with the present application.

With reference to FIG. 9, a magnetic resonance scanner 10 includes a scanner housing 12 in which a patient 16 or other subject is at least partially disposed with a heart or other organ or anatomical region to be studied positioned in a scanning region 18 of the scanner 10. Although described with reference to a bore-type scanner, it is to be appreciated that the scanner could also be an open-magnet scanner or other type of magnetic resonance scanner. A main magnet 20 disposed in the scanner housing 12 is controlled by a main magnet controller 22 to generate a static ($B_0$) magnetic field in at least the scanning region 18. Typically, the main magnet 20 is a persistent superconducting magnet surrounded by cryoshrouding 24, although a resistive magnet can also be used. In some embodiments, the main magnet 20 generates a main magnetic field of between about 0.23 Tesla and about 7 Tesla; however, main magnetic fields of strengths above or below this typical range are also contemplated. A gradient system including magnetic field gradient coils 26 arranged in or on the housing 12 and corresponding gradient controllers 28 superimpose selected magnetic field gradients on the main magnetic field in at least the scanning region 18. Typically, the magnetic field gradient coils 26 include coils for producing three orthogonal magnetic field gradients, such as x-, y-, and z-gradients.

A generally cylindrical whole-body coil 30 is mounted substantially coaxially with the bore of the magnetic resonance scanner 10. The whole-body coil 30 may be, for example, a quadrature birdcage coil, transverse electromagnetic (TEM) coil, or so forth. Additionally or alternatively, one or more local radio frequency coils such as a surface coil or plurality of surface coils, a SENSE coil array, a torso coil, or so forth (not shown) can be employed. In the embodiment of FIG. 9, the whole-body coil 30 performs both transmit and receive functions. That is, the whole-body coil 30 is energized at a magnetic resonance frequency by one or more radio frequency transmitters 32 to excite magnetic resonance in the subject 16, and the whole-body coil 30 is also used in conjunction with one or more radio frequency receivers 34 to receive magnetic resonance signals emanating from the subject 16 responsive to such excitation. Suitable radio frequency switching circuitry 36 are provided to enable the whole-body coil 30 to perform both transmit and receive functions.

While shown as a separate unit, in some embodiments the radio frequency switching circuitry or portions thereof may be integrated into the whole-body coil, the radio frequency transmitter, or the radio frequency receiver. In other contemplated embodiments, the whole-body coil 30 performs the transmit function, while one or more local radio frequency coils receives the generated magnetic resonance signals. In other contemplated embodiments, the whole-body coil 30 is omitted and one or more local radio frequency coils perform both transmit and receive functions. It is still further contemplated to use the whole-body coil 30 as a receive coil while magnetic resonance is excited using one or more local radio frequency coils.

The magnetic resonance scanner 10 operates under the control of a scanner controller 40 to perform a selected magnetic resonance sequence 42, such as the example T1 mapping sequence as shown in FIG. 10. As stated above, the exemplary embodiment utilizes CMR T1 mapping using a MOLLI sequence prior and at ten, twenty, and thirty minutes following contrast administration. However, it should be appreciated that other magnetic resonance sequences such at T2 mapping and the like can be utilized. A user interface 44 enables a radiologist or other user to select the sequence 42 or another magnetic resonance sequence, and also enables the user to set or modify parameters of the sequence such as a $T_S$ temporal offset parameter of the example T1 mapping sequence 42. With continuing reference to FIG. 9 and with further reference to FIG. 10, the example T1 study protocol 42 is described in greater detail. The sequence 42 starts with the acquisition of survey image(s) 80 followed by planning image(s) 82. Native T1 image(s) 84 are acquired before a contrast agent is administered 86. After the contrast agent is administered 86, a short-axis stack of images 88 is acquired. Ten minutes after administration of the contrast agent, a second set of T1 image(s) 90 are acquired. Following acquisition of the second set of T1 image(s) 90, a transverse stack of image(s) 92 are acquired. Twenty minutes after administration of the contrast agent, a third set of T1 image(s) 94 are acquired. Following acquisition of the third set of T1 image(s) 94, one or more scar images 96 are acquired. Thirty minutes after administration of the contrast agent, a fourth set of T1 image(s) 98 are acquired. Rather, in another exemplary embodiment, virtually any other accurate T1 mapping sequence can be used instead of MOLLI. In the exemplary method, the MOLLI sequence produces 11 images that can be used for T1 map reconstruction.

The scanner 10 operates under the control of the scanner controller 40 in accordance with the selected sequence 42 to excite magnetic resonance and generate magnetic resonance data that are stored in a data memory or buffer 46. The sequence is re-executed to generate multiple sets of data, such as the illustrated $T_{S1}$ dataset, $T_{S2}$ dataset, ... shown in the data buffer 46 corresponding to re-executing the selected sequence 42 with different values for the temporal offset parameter $T_S$. Optionally, an electrocardiograph 50 with leads 52, or additional or other auxiliary equipment, monitors the patient 16 during the magnetic resonance data acquisition. For example, the ECG 50 can provide cardiac gating information to ensure that data is acquired at about a selected cardiac phase such as at about the diastolic phase or about the systolic phase. In some embodiments, the generating of saturation recovery or inversion recovery data is cardiac gated using the ECG 50 such that data are acquired in multiple cardiac phases, and multiple saturation recovery or inversion recovery data sets are derived, in which each data set is assigned to a selected cardiac phase.

A reconstruction processor 70 reconstructs the acquired magnetic resonance data into a reconstructed image. In the illustrated embodiment, each re-execution of the T1 mapping sequence 42 generates a separate informational magnetic resonance dataset, such as datasets acquired with a temporal offset parameter $T_S$ having values $T_{S1}$ and $T_{S2}$, respectively, for successive executions of the sequence 42. These datasets are each reconstructed into a reconstructed image by the reconstruction processor 70, so as to for example generate reconstructed $T_{S1}$ and $T_{S2}$ images, and so forth, which are suitably stored in an images memory or buffer 72. Processing in addition to or instead of image reconstruction can also be performed on the informational magnetic resonance data. For example, the reconstructed images acquired using the T1 mapping sequence 42 are suitably processed by a T1 mapping processor 74 to generate a T1 map of the imaged region. The T1 map is suitably displayed on the user interface 44 or on another display device, or may be printed, communicated over the Internet or a local area network, stored on a non-volatile storage medium, or otherwise used. In the example configuration illustrated in FIG. 9, the user interface 44 performs both scanner control interfacing and data display and analysis tasks; however, it is also contemplated to have separate scanner control interfacing and data display and/or analysis computers or systems. In one embodiment, the T1 mapping processor 74 corrects for motion of the reconstructed images before generation of the T1 map of the imaged region. In accordance with an exemplary method described herein, a hierarchical adaptive local affine registration (HALAR) technique can be used. In another exemplary method in accordance with the present application, virtually any other accurate motion correction technique can be used.

A T1 value processor 76 extracts values from the T1 map of the imaged region and checks for a correlation between the patient's heart rate (HR) and the T1 values. For example, the electrocardiograph 50 with leads 52 provides heart rate information during the magnetic resonance data acquisition. One approach that can be used in accordance with exemplary embodiments of the present application is to check for a correlation between HR and T1 and then normalize T1 values to average study HR using that correlation. The T1 value processor 76 also calculates an average T1 and R1 inside a region of interest (ROI). R1 values are the inverse of the T1 values. In one embodiment, a radiologist or other user selects the ROI utilizing the user interface 44. For example, a mid-septal ROI can be selected via the user interface and the average T1 and R1 calculated inside the ROI. The ROI can be determined automatically in another embodiment, for example.

The T1 value processor 76 also differentiates the ROI between diseased and normal tissue. Specifically, the T1 value processor 76 compares the average T1 values in the ROI to cut-off T1 value to diagnose the ROI. If the average T1 values in the TOI are below the cut-off T1 value, the tissues within the ROI are deemed healthy. If the average T1 values in the ROI are above the cut-off T1 value, the tissues within the ROI are deemed diseased. In the exemplary embodiment, a cut off value of 1184 ms on native T1 maps is suitable to distinguish between diseased and normal tissue in the ROI. For example, using the exemplary method described herein, it is possible to identify the native T1 value as the independent discriminator of cardiomyopathic myocardium (p=0.001) with a sensitivity of 100%, specificity 96%, diagnostic accuracy 99%, and a positive predictive value of 98% and a negative predictive value of 100%. In connection with SLE patients, exemplary methods described herein yielded results including prolonged native T1 (cut-off value 1108 ms), providing means to detect sublicinical involvement in SLE patients with high diagnostic accuracy (sensitivity of 100%, specificity 91%, diagnostic accuracy 95%), for example. The resulting diagnosis from the comparison of the average T1 values to the cut-off T1 values are then displayed on the user interface 44. It should also be appreciated that a radiologist or other user can change the cut-off T1 value utilizing the user interface 44.

While the components of a magnetic resonance scanner 10 were shown as independent components, it is to be appreciated that each of the components can be part of a magnetic resonance scanner system. At least some of the components of magnetic resonance scanner 10 each include at least one processor executing computer executable instructions from at least one memory thereof. The computer executable instructions embody the functionality of the components and include the applications of magnetic resonance scanner 10. Further, at least some of the components each include a communication unit and/or at least one system bus. A communications unit provides a corresponding processor with an interface to at least one communication network, such as the communication network. A system bus allows the exchange of data between sub-components of the components. Sub-components include processors, memories, sensors, display devices, communication units, and so on.

With reference to FIG. 11, a block diagram of a method for differentiation of normal myocardium from diffuse disease using T1 mapping is illustrated. In a step 100, one or more images of a patient are acquired by an imaging apparatus. In a step 102, the motion of the images is corrected. In a step 104, a T1 map is generated from the one or more images. In a step 106, T1 values are extracted from the T1 map. In a step 108, the T1 values are corrected for the heart rate of the patient. In a step 110, a region of interest is defined within the T1 map. In a step 112, the average T1 value within the region of interest is calculated. In a step 114, the average T1 value within the region of interest is compared to a cut-off T1 value. In a step 116, a diagnosis of tissue within the region of interest is determined from the comparison.

Exemplary systems and methods described herein applied to myocardial T1 native can provide the greatest distinction between healthy myocardium and diseased with high negative predictive value. Accordingly, there is significant potential for development of easy-to-implement tests in patients with suspected diffuse fibrosis, which may be missed by classic LGE imaging procedures. Furthermore, in subjects with low pretest likelihood for the presence of cardiomyopathy (descriptive of an exemplary control group), or in those where contrast administration is contraindicated, exemplary embodiments according to the present application can serve as an effective screening test. One having ordinary skill in the art should appreciate in view of the teachings herein that there are many other clinical applications for which exemplary systems and methods described herein and in accordance with the present application can be used.

Further, as one having ordinary skill in the art will appreciate in view of the teachings provided herein, features, elements, components, etc. described in the present disclosurespecification (and in related 61/613,626) and/or depicted in the appended Figures and/or any other Appendixes, may be implemented in various combinations of hardware and software, and provide functions which may be combined in a single element or multiple elements. For example, the functions of the various features, elements, components, etc. shownillustrateddepicted in the Figures can be provided through the use of dedicated hardware as well as hardware capable of executing software in association with appropriate software. When provided by a processor, the functions can be provided by a single dedicated processor, by a single shared processor, or by a plurality of individual processors, some of which can be shared and/or multiplexed. Moreover, explicit use of the term "processor" or "controller" should not be construed to refer exclusively to hardware capable of executing software, and can implicitly include, without limitation, digital signal processor ("DSP") hardware, memory (e.g., read-only memory ("ROM") for storing software, random access memory ("RAM"), non-volatile storage, etc.) and virtually any means and/or machine (including hardware, software, firmware, combinations thereof, etc.) which is capable of (and/or configurable) to perform and/or control a process.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (e.g., any elements developed that can perform the same or substantially similar function, regardless of structure). Thus, for example, it will be appreciated by one having ordinary skill in the art in view of the teachings provided herein that any block diagrams presented herein can represent conceptual views of illustrative system components and/or circuitry embodying the principles of the invention. Similarly, one having ordinary skill in the art should appreciate in view of the teachings provided herein that any flow charts, flow diagrams and the like can represent various processes which can be substantially represented in computer readable storage media and so executed by a computer, processor or other device with processing capabilities, whether or not such computer or processor is explicitly shown.

Furthermore, exemplary embodiments of the present invention can take the form of a computer program product accessible from a computer-usable and/or computer-readable storage medium providing program code and/or instructions for use by or in connection with, e.g., a computer or any instruction execution system. In accordance with the present disclosure, a computer-usable or computer readable storage medium can be any apparatus that can, e.g., include, store, communicate, propagate or transport the program for use by or in connection with the instruction execution system, apparatus or device. Such exemplary medium can be, e.g., an electronic, magnetic, optical, electromagnetic, infrared or semiconductor system (or apparatus or device) or a propagation medium. Examples of a computer-readable medium include, e.g., a semiconductor or solid state memory, magnetic tape, a removable computer diskette, a random access memory (RAM), a read-only memory (ROM), flash (drive), a rigid magnetic disk and an optical disk. Current examples of optical disks include compact disk read only memory (CD-ROM), compact disk readwrite (CD-RW) and DVD. Further, it should be understood that any new computer-readable medium which may hereafter be developed should also be considered as computer-readable medium as may be used or referred to in accordance with exemplary embodiments of the present invention and disclosure.

Having described preferred and exemplary embodiments for systems, devices and methods pertaining to differentiation of normal myocardium from diffuse disease using T1 mapping in non-ischemic cardiomyopathies and others, for example (which embodiments are intended to be illustrative and not limiting), it is noted that modifications and variations can be made by persons skilled in the art in light of the teachings provided herein, including the Figures and Appendixes. It is therefore to be understood that changes can be made into the preferred and exemplary embodiments of the present application which are within the scope of the embodiments described herein. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A magnetic resonance system comprising:
   a magnetic resonance imaging apparatus; and
   one or more processors programmed to:
   receive one or more images of a heart of a patient acquired by the magnetic resonance imaging apparatus;
   generate a T1 map from the one or more images;
   define a region of interest within the one or more images;
   determine the average T1 value within the region of interest;
   compare the average T1 value within the region of interest to a cut-off T1 value; and
   determine a hypertrophic cardiomyopathy (HCM) or non-ischemic dilated cardiomyopathy (DCM) diagnosis of the region of interest from the comparison;
   wherein the one or more images of the heart of the patient are acquired only without contrast agent and the generated T1 map is a native T1 map.

2. The magnetic resonance system according to claim 1, wherein the one or more processors are further programmed to perform:
   a motion correction of the T1 mapping; and
   a heart rate correction of the T1 values.

3. The magnetic resonance system according to claim 1, wherein the T1 mapping utilizes a Modified Look-Locker Inversion imaging sequence.

4. The magnetic resonance system according to claim 1, wherein the heart rate correction includes:
   checking for a correlation between heart rate of the patient and T1 values; and
   normalizing the T1 values using the correlation.

5. The magnetic resonance system according to claim 1, wherein the HCM or non-ischemic DCM diagnosis for an average T1 value above the cut-off T1 value is disease and the HCM or non-ischemic DCM diagnosis for an average T1 value below the cut-off T1 value is healthy.

6. The magnetic resonance system according to claim 1, wherein the cut-off T1 value is 1184 ms.

7. The magnetic resonance system according to claim 1, wherein the region of interest is the myocardium or part of the myocardium.

8. A magnetic resonance system, comprising:
   an imaging apparatus which acquires one or more images of a patient without contrast agent present;
   a T1 mapping processor which generates a native T1 map from the one or more images; and
   a T1 value processor which defines a region of interest within the one or more images, determines the average T1 value within the region of interest, compares the average T1 value within the region of interest to a cut-off T1 value, and provides a diagnosis based on the comparison;
   wherein a diagnosis for an average T1 value below the cut-off T1 value is healthy.

9. The system according to claim 8, wherein the T1 mapping processor further corrects for at least one of motion of the T1 map and T1 values for heart rate.

10. The system according to claim 8, wherein the T1 mapping utilizes a Modified Look-Locker Inversion imaging sequence.

11. The system according to claim 8, wherein the heart rate correction includes:
    checking for a correlation between heart rate of the patient and T1 values; and
    normalizing the T1 values using the correlation.

12. The magnetic resonance system according to claim 8, wherein the region of interest is the myocardium or part of the myocardium.

13. A method for differentiation of normal myocardium from diffuse disease using T1 mapping, the method comprising, with at least one electronic processor:
    acquiring one or more magnetic resonance signals from a patient without contrast agent using a magnetic resonance imaging apparatus;
    reconstructing the received MR signals into one or more images of a patient;
    generating a native T1 map without contrast from a contrast agent from the one or more images;
    defining a region of interest within the one or more images;
    determining the average T1 value within the region of interest;
    comparing the average T1 value within the region of interest to a cut-off T1 value; and
    determining a diagnosis of the region of interest from the comparison, wherein the diagnosis for an average T1 value above the cut-off T1 value is hypertrophic cardiomyopathy (HCM) or non-ischemic dilated cardiomyopathy (DCM) disease and the diagnosis for an average T1 value below the cut-off T1 value is healthy.

14. The method according to claim 13, further including, with the at least one electronic processor:
    correcting for motion the T1 mapping; and
    correcting for heart rate of the T1 values.

15. The method according to claim 13, wherein the T1 mapping utilizes a Modified Look-Locker Inversion imaging sequence.

16. The method according to claim 13, wherein the region of interest is the myocardium or part of the myocardium.

* * * * *